(12) United States Patent
Panchbahavi (10) Patent No.: US 8,828,000 B2
(45) Date of Patent: Sep. 9, 2014

(54) APPARATUS TO TRACE AND CUT A TENDON OR OTHER LATERALLY EXTENDED ANATOMICAL STRUCTURE

(75) Inventor: Vinod Kumar Panchbahavi, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1442 days.

(21) Appl. No.: 12/030,781

(22) Filed: Feb. 13, 2008

(65) Prior Publication Data

US 2008/0221579 A1   Sep. 11, 2008

Related U.S. Application Data

(60) Provisional application No. 60/889,581, filed on Feb. 13, 2007.

(51) Int. Cl.
| *A61B 17/00* | (2006.01) |
| *A61B 17/32* | (2006.01) |
| *A61B 18/18* | (2006.01) |
| *A61B 17/10* | (2006.01) |

(52) U.S. Cl.
CPC ........... *A61B 17/32* (2013.01); *A61B 17/00008* (2013.01); *A61B 17/320016* (2013.01); *A61B 2017/320052* (2013.01); *A61B 2017/00969* (2013.01); *A61B 2017/320056* (2013.01)
USPC .......................................................... 606/79

(58) Field of Classification Search
USPC ...................................... 606/79–85, 103, 104
See application file for complete search history.

(56) References Cited

U.S. PATENT DOCUMENTS

| 5,681,324 | A | * | 10/1997 | Kammerer et al. | 606/113 |
| 5,961,530 | A | * | 10/1999 | Moore et al. | 606/148 |
| 6,068,642 | A | * | 5/2000 | Johnson et al. | 606/180 |
| 6,423,071 | B1 | * | 7/2002 | Lawson | 606/103 |
| 6,440,138 | B1 | * | 8/2002 | Reiley et al. | 606/79 |
| 6,752,814 | B2 | * | 6/2004 | Gellman et al. | 606/148 |
| 7,553,307 | B2 | * | 6/2009 | Bleich et al. | 606/1 |
| 7,857,813 | B2 | * | 12/2010 | Schmitz et al. | 606/79 |
| 2003/0065335 | A1 | * | 4/2003 | Guido et al. | 606/144 |
| 2004/0211434 | A1 | * | 10/2004 | Loomas et al. | 128/898 |
| 2007/0055262 | A1 | * | 3/2007 | Tomita et al. | 606/82 |
| 2007/0123888 | A1 | * | 5/2007 | Bleich et al. | 606/79 |

* cited by examiner

*Primary Examiner* — Christopher Beccia
(74) *Attorney, Agent, or Firm* — Wong, Cabello, Lutsch, Rutherford & Brucculeri, LLP.

(57) ABSTRACT

A harvesting apparatus is disclosed for harvesting anatomical structures such as tendons, fine muscles, nerves and blood vessels, where the apparatus includes an elongate member having two longitudinally extending tubes or tubular apertures extending from the member's proximal end to its distal end. The distal end includes opposing heads and an arcuate base. The anatomical structure is placed on the arcuate base and a flexible cutting member is threaded through one tube over the anatomical structure and into and through the other tube. The elongate member is then directed into an animal or human body along the structure to a position where the anatomical structure is to be cut. Then the cutting member is pulled back and forth at the distal end causing into to cut the anatomical structure at the distal head.

18 Claims, 9 Drawing Sheets

APPARATUS TO TRACE AND CUT A TENDON OR OTHER LATERALLY EXTENDED ANATOMICAL STRUCTURE

RELATED APPLICATIONS

This application claims priority to and the benefit of U.S. Provisional Patent Application Ser. No. 60/889,581 filed 13 Feb. 2007.

BACKGROUND OF THE INVENTION

1. Field of the Invention

The present invention relates to an apparatus for tracing and cutting a laterally extending anatomical structure in an animal's body including a human body and to methods for making and using same.

More particularly, the present invention relates to an apparatus for tracing and cutting a laterally extending anatomical structure in an animal's body including a human body, where the apparatus includes an elongate flexible body having a proximal end, a distal end, a cutting member extending from the proximal end to the distal end and back through tubes in the flexible body terminating at two opposing apertures in two opposing cutting guides. The apparatus is ideally suited for harvesting tendons or other laterally extending anatomical structures from a surgically accessible point to a desired cutting point along the tendon or other structure within the animal or human body. The present invention also relates to methods for making and using same.

2. Description of the Related Art

The flexor digitorum longus (FDL) and flexor hallucis longus (FHL) tendons are used in a variety of foot reconstructive procedures. These tendons are generally harvested from the midfoot and transferred to a different location in the foot to augment or replace a degenerated tendon.

The FDL is transferred to the navicular bone in treatment of stage II dysfunction of the posterior tibial tendon. The FUL also is used, but less commonly for this purpose. The FHL tendon is more commonly used for Achilles tendon dysfunction caused by chronic tear or degeneration.

With the open operative technique for harvest of the FDL described by Mann and Thompson in J. Bon Joint Surg. 67-A: 556-561, 1985, the FDL sheath is identified at the medial malleolus and followed distally. The abductor hallucis muscle is refracted plantarward to expose the interval between the flexor hallucis brevis and the first metatarsal. The origin of the flexor hallucis brevis muscle is released to increase the exposure of the plantar aspect of the foot. The FDL tendon sheath is opened, and the tendon kept an tension, while the dissection of the sheath is carried distally into the planatar aspect of the foot. As dissection progresses, a number of vessels have to be cauterized. The FDL tendon is sharply divided at the most edistal extent possible. A formal tenodesis of the FEL stump and the FHL distally is not considered necessary because of communicating tendinous slips between the FDL and FHL. This "open" technique requires extensive, deep, and difficult, dissection in the midfoot in the vicinity of blood vessels and nerves.

To improve the success of this technique, the inventor has developed a "minimally invasive" augmented technique. The tendon sheath of the FDL or FHL is identified in the region of the hindfoot through the exposure used for the index procedure, such as exploration of the posterior tibial tendon or the Achilles tendon.

Figure 1A:
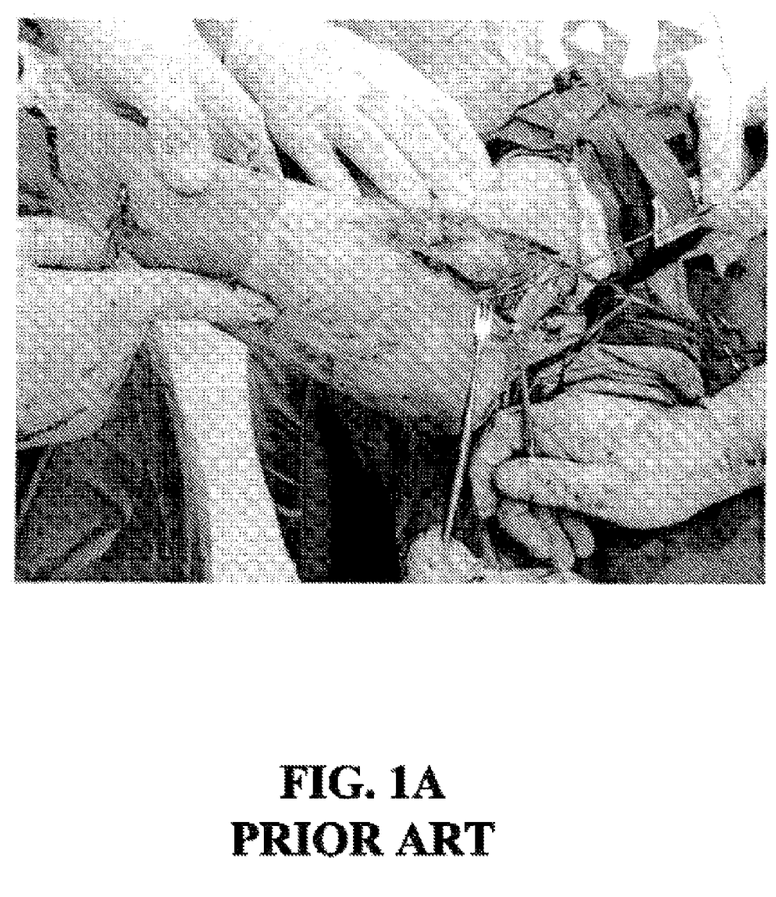
FIGS. 1A-C depict photographs of a prior art instrument and method for extracting a tendon for transplantation.
Figure 1B:
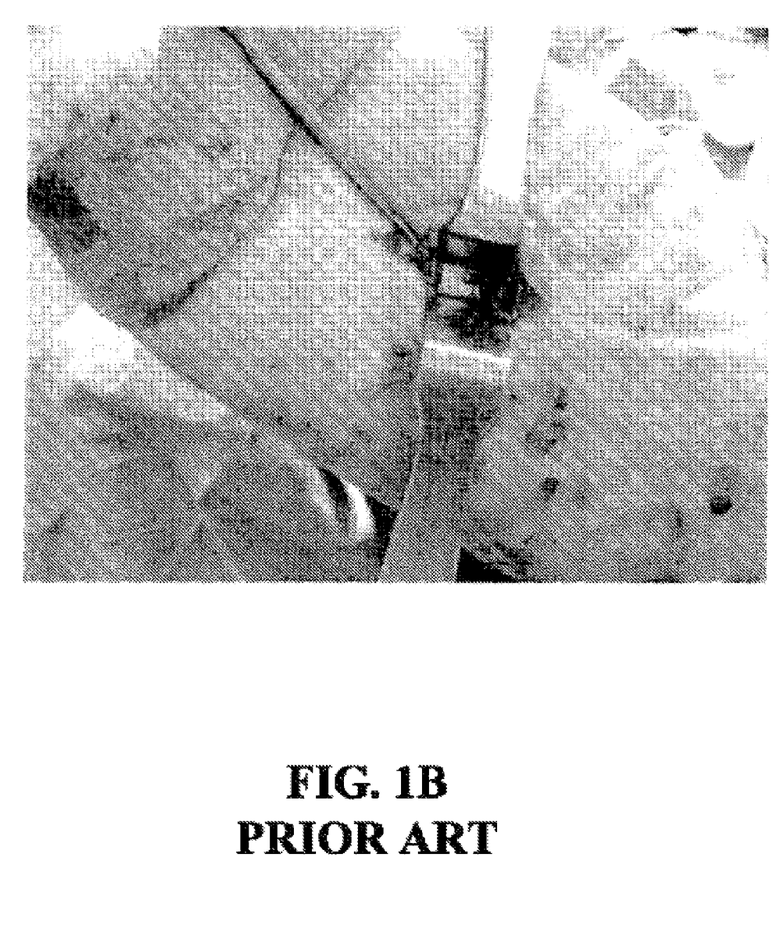

A malleable metallic probe that has a smooth bulb at its tip is introduced within the tendon sheath and passed gently distally into the midfoot where it is easily palpated as shown in FIG. 1A. A vertical incision is then made in the skin of the midfoot over the prominence made by the probe. Once the skin is incised, the central part of the plantar aponeurosis is exposed. The vertically oriented fibers of the aponeurosis are separated to expose muscle fibers of the flexor digitorum brevis muscle. These muscle fibers are then separated and retracted to expose the FDL tendon as shown in FIG. 1B. Because the lateral branch of the medial plantar nerve passes close to the medial border of the flexor digitorum brevis and could be at risk, it is important to make the plantar incision long enough to allow adequate visualization. The identity of the tendon is verified by pulling on the tendon through the proximal incision in the hindfoot and assessing transmission of the tension distally to the tendon in the midfoot and at the same time observing maximal flexion in either the lesser toes or greater toe.

Figure 1C:
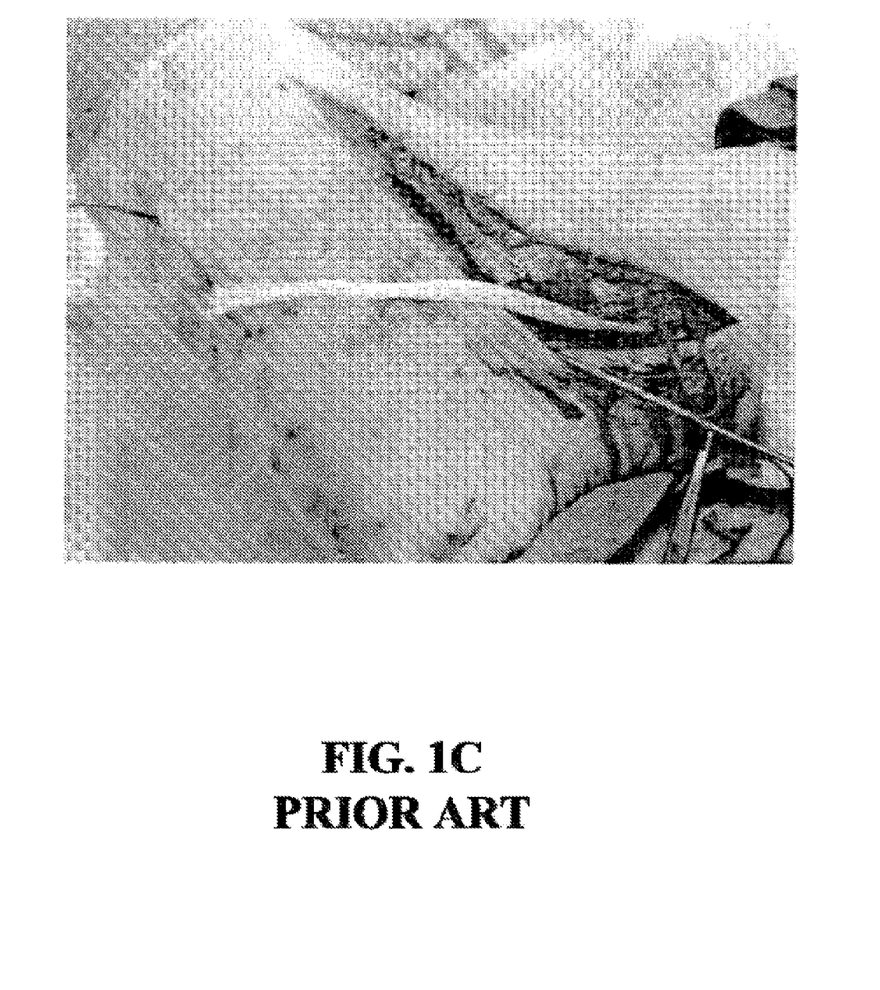

The tendon is then cut sharply in the midfoot and the cut end pulled proximally through the incision in the hindfoot as shown in FIG. 1C.

However, even with the augment technique, the technique involves an additional surgical procedure in a very sensitive area of the foot increasing post operative problems. Thus, there is a need in the art for an apparatus that can be used to harvest tendon and other laterally extending anatomical structures in an animal's body including a human body that does not require additional surgical incisions.

SUMMARY OF THE INVENTION

The present invention provides a harvesting apparatus including an elongate flexible body. The body includes a proximal end, a distal end and a flexible cutting member. The body includes two hollow tubular members extending a length of the body from the proximal end to the distal end. The tubular members run parallel down the length of the body from the proximal end to a point near the distal end. In one embodiment, the distal end includes two opposing cutting guide heads having opposing cutting channels. The distal end also includes an arcuate base between the two heads adapted to receive an anatomical structure. The cutting member is adapted to be threaded into one tubular aperture at the proximal end of the body until it exits through its cutting guide head so that the cutting member is positioned above or rests adjacent a top surface of the structure to be cut. In another embodiment, the distal end includes two opposing cutting guide heads defining a slot for receiving an anatomical structure. The distal end is generally flat, but when an anatomical structure is inserted into the distal end, the distal end flexes up. This tension provides the downward force for cutting through the anatomical structure so that the distal end will relax to its generally flat configuration.

The cutting member is then threaded through the other tubular aperture until it exits the other tubular aperture at the proximal end of the body. The threading can be performed prior to positioning the structure in the distal end or after positioning the structure in the distal end. The distal end of the apparatus is then pushed or slid along the structure until the distal end is positioned at a location along the structure, where the structure is to be cut. By alternately pulling on the cutting member ends, the cutting member will follow the channel and cut the structure section positioned between the two cutting guide heads. In certain embodiments, the channels are angled so that a top of the channel is more distal than a bottom of the channel to increase cutting efficiency. In certain embodiments, a top surface of the body of the apparatus is curved to engage and aid the apparatus body in following the anatomical structure to the point where the structure is to be cut. The apparatus is ideally suited for harvesting tendons or other laterally extending anatomical structures from a surgically accessible point to a desired cutting point along the tendon within the animal or human body. In those embodiments, where the distal end does not include cutting channels, but cuts due to a force to attain a flat contour and the end expands to allow the anatomical structure to be cut, the back and forth motion of the cutting member cuts through the structure.

The present invention also provides a harvesting apparatus including an elongate flexible body. The body includes a proximal end, a distal end, a flexible cutting member, and a flexible, bio-erodible or bio-degradable suturing member. The body includes three tubular apertures extending a length of the body from the proximal end to the distal end. The tubular apertures run parallel down the length of the body from the proximal end to a point near the distal end. The distal end includes a suturing station and a cutting station. The suturing station includes two opposing suturing heads, an arcuate suturing base between the suturing heads and a suture guide channel extending from the suturing heads to the heads, where the base is adapted to receive an anatomical structure so that the suturing member loops around the structure. The suturing member is designed to be threaded through the tubular aperture leading to the suturing station and fitted into the suture guide channel and across a top surface of the anatomical structure. The suture member is then tied off at the other head with a slip knot so that when the suturing member is pulled at the proximal end of the apparatus, the loop will tighten on the structure sealing the structure at the suturing station. The cutting station includes two opposing cutting guide heads having opposing cutting channels. The cutting station also includes an arcuate base between the two heads adapted to receive the anatomical structure so that the cutting member is positioned above and rests adjacent a top surface of the structure. The cutting member is adapted to be threaded into one tubular aperture at the proximal end of the body until it exits through its cutting guide head. The cutting member is then threaded into and through the other tubular aperture until it exits the other tubular aperture at the proximal end of the body. By alternately pulling on the cutting member ends, the cutting member will follow the channel and cut the structure portion positioned between the two cutting guide heads proximate the sutured portion of the structure. In certain embodiments, the channels are angled so that a top of the channel is more distal than a bottom of the channel to increase cutting efficiency. In certain embodiments, a top surface of the body of the apparatus is curved to engage and aid the apparatus body in following the anatomical structure to the point where the structure is to be cut. The apparatus is ideally suited for harvesting blood vessels or other tubular structures from a surgically accessible point to a desired cutting point along the tendon within the animal or human body.

Any of the above embodiments can also include fiber optic systems for light and viewing the positioning of the distal end of the apparatus. The distal end of the apparatus can also include X-ray opaque elements for X-ray monitoring of distal end positioning. The distal end of the apparatus can also include monitors for monitoring an environment surrounding the distal end. The distal end can also include ultrasound reflective elements for ultrasound monitoring of distal end position.

The present invention provides a method for harvesting a laterally extending anatomical structure of an animal including a human. The method includes the step of making an incision in the animal or human at a convenient location to expose the anatomical structure to be harvested. The distal end of an apparatus of this invention is then positioned so that the structure rests on the arcuate base between the cutting head or on the two arcuate bases of the suturing station and the cutting station. Once the distal end is properly positioned on the structure, the cutting member is inserted into one of the tubular apertures and threaded through the aperture until it exits at one of the cutting heads. The cutting member is then passed over the structure and into the other tubular aperture at the opposing cutting head and threaded through the tubular aperture until it exits the tubular aperture at the proximal end of the apparatus. The distal end of the apparatus is then forced along the structure from the incision to a position along the structure in the animal or human, where the structure is to be cut. The cutting member is then pulled from one end and then from the other end causing the cutting member to cut into and through the structure at the distal end. After the structure is severed at the distal end, the apparatus is withdrawn along with the cut structure.

The present invention provides a method for harvesting a laterally extending anatomical structure of an animal including a human. The method includes the step of making an incision in the animal or human at a convenient location to expose the anatomical structure to be harvested. The distal end of an apparatus of this invention is then positioned so that the structure rests on the arcuate base between the cutting head or on the two arcuate bases of the suturing station and the cutting station. Once the distal end is properly positioned on the structure, then for those apparatuses with suturing stations, the suturing member is inserted into the suturing tubular aperture until the suturing member exits the end of the suturing tubular aperture at the suturing station. The suturing member is then threaded through the suturing channel until is loops around the structure. A slip knot is then formed in the suturing member and the knot forced into the suturing channel so that it remains there until the suturing member is pulled at the proximal end of the apparatus causing the loop to tighten around the structure and sealing the structure at the suturing station. The cutting member is inserted into one of the tubular apertures and threaded through the aperture until it exits at one of the cutting heads. The cutting member is then passed over the structure and into the other tubular aperture at the opposing cutting head and threaded through the tubular aperture until it exits the tubular aperture at the proximal end of the apparatus. The distal end of apparatus is then forced along the structure from the incision to a position along the structure in the animal or human, where the structure is to be suture and cut. The suturing member is then pulled to suture the structure at the suturing station. Once the structure has been sutured, the cutting member is then pulled from one end and then from the other end causing the cutting member to cut into and through the structure at the distal end. After the structure is severed at the distal end, the apparatus is withdrawn along with the cut structure.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that an apparatus can be constructed to harvest anatomical structures such as tendons, slender muscles, long nerve filaments or bundles, blood vessels, or other laterally extended anatomical structures. The apparatus includes an elongate body having proximal end and a distal end. The distal end includes two opposing cutting guides and an arcuate base adapted to partially surround an anatomical structure positioned with the base. The apparatus includes a flexible cutting member adapted to be threaded through two tubular apertures, each extending from the proximal end to each of the cutting guides of the distal end. When the cutting member is threaded through the tubular members, a portion of the cutting member will rest on a top surface of a portion of the anatomical structure. Once the distal end is positioned at a point on the structure where the structure will be cut, cutting can commence. By alternatively pulling the ends of the cutting member, the member will follow guide channels in the guide heads and cut through the tendon. In certain embodiments, the cutting guides are angled so that when the cutting member is at the top of the guide channels it is farther from the proximal end and closer at the bottom of the guides channels. The angle is generally between about 5° and about 75° from the vertical (taken as 0° here). In other embodiments, the distal end assembly does not include channels, but the distal end assembly prefers to be generally flat, but when the structure is inserted into the distal end assembly, the assembly is flexed. The downward pressure on the structure provides the force that permits the cutting member to cut the structure.

The invention broadly relates to an apparatus including an elongate member including a proximal end and a distal end. The apparatus also include a flexible cutting member in the form of a string or wire. The elongate member includes two tubular apertures extending from the proximal end of the apparatus to a location in the distal end. The distal end includes two opposing cutting guide heads and an arcuate base extending between or interposed between the opposing cutting heads. The tubular apertures terminate at a base of cutting grooves that extend to a top location of the cutting heads so that when an anatomical structure is properly position in the arcuate base of the distal end, the cutting member extends across a gap between the cutting heads proximate a top of the structure or resting on the top of the structure. The cutting member is adapted to be inserted into one of the tubular apertures at the proximal end of the apparatus and threaded through the aperture until it exits at the base of its groove. The cutting member is then passed up over the structure along the grooves and into the other tubular aperture. The cutting member is then threaded through the second aperture and out of the proximal end of the apparatus. The distal end of the apparatus is then forced along the structure until the distal end is properly positioned at a location to be cut. Once properly positioned, the structure is cut by pulling alternate ends of the cutting member back and forth cutting the structure. The cutting member can flow along guide channels in the distal end.

The present invention also relates to a harvesting apparatus comprising an elongate flexible body including a proximal end, a distal end, two hollow tubular members extending a length of the body and having two opposing distal cutting guide heads disposed at the distal end of the body and two proximal openings disposed at or near the proximal end of the body. The apparatus also comprises a flexible cutting member adapted to be threaded into one tubular member through its proximal opening, through the tubular member, out its guide head, into the other tubular member through its guide head, through the other tubular member, and out it its proximal opening. The distal end is adapted to receive an anatomical structure and a back and forth motion of the cutting member results in severing of the anatomical structure. In certain embodiments, the tubular members further have opposing cutting channels. In other embodiments, the tubular members further have an arcuate base between the two heads adapted to receive an anatomical structure. In other embodiments, the channels are angled so that a top of the channel is more distal than a bottom of the channel to increase cutting efficiency. In certain embodiments, a top surface of the body of the apparatus is curved to engage and aid the apparatus body in following the anatomical structure to the point where the structure is to be cut. In other embodiments, the proximal end of the body comprises a handle. The anatomical structure is a tendon, a slender muscle, a long nerve filament or bundle, a vessel, or other laterally extended anatomical structures. In any of the embodiments of this paragraph, the he apparatus may also comprise a fiber optic system for viewing the positioning of the distal end of the apparatus, X-ray opaque elements for X-ray monitoring of distal end positioning, ultrasound reflective elements for ultrasound monitoring of distal end position, or a monitor for monitoring an environment surrounding the distal end.

The present invention also relates to an harvesting apparatus comprising an elongate flexible body. The elongate body includes three tubular members extending a length of the body, each member having proximal openings. The elongate body also includes a distal end comprising a suturing station. The suturing station comprises two opposing suturing heads, a suture guide channel extending from the suturing heads, and an arcuate suturing base between the suturing heads, where the base is adapted to receive an anatomical structure so that the suturing member loops around the structure, where the suturing member is designed to be threaded through the tubular aperture leading to the suturing station and fitted into the suture guide channel and across a top surface of the anatomical structure. The elongate body also includes a cutting station comprising two opposing distal cutting guide heads. The distal end of the body is adapted to receive an anatomical structure and a back and forth motion of the cutting member results in severing of the anatomical structure. The apparatus also includes a flexible cutting member adapted to be threaded into one of the three tubular members through its proximal opening, through the tubular member, out its guide head, into a second of the three tubular member through its guide head, through the second tubular member, and out it its proximal opening. The apparatus also includes a flexible, bio-erodible or bio-degradable suturing member threaded through the third tubular member forming a loop at the suturing station and tied off at one of the suturing heads with a slip knot so that when the suturing member is pulled at its proximal end extending out of the proximal opening of the third tubular member, the loop will tighten on the anatomical structure suturing the structure at the suturing station. In certain embodiments, the cutting station further comprises opposing cutting channels. In other embodiments, the cutting station further comprises an arcuate base between the two heads adapted to receive an anatomical structure. In other embodiments, the channels are angled so that a top of the channel is more distal than a bottom of the channel to increase cutting efficiency. In other embodiments, a top surface of the body of the apparatus is curved to engage and aid the apparatus body in following the anatomical structure to the point where the structure is to be cut. In other embodiments, the proximal end of the body comprises a handle. In other embodiments, the anatomical structures is a tendon, a slender muscle, a long nerve filament or bundle, a vessel, or other laterally extended anatomical structures. In any of the embodiments of this paragraph, the apparatus may also comprise a fiber optic system for viewing the positioning of the distal end of the apparatus, X-ray opaque elements for X-ray monitoring of distal end positioning, ultrasound reflective elements for ultrasound monitoring of distal end position, or a monitor for monitoring an environment surrounding the distal end.

The present invention also relates to a method for harvesting a laterally extending anatomical structure of an animal including a human, the method comprising the step of making an incision in the animal or human at a convenient location to expose an anatomical structure to be harvested. After the incision is made, a distal end of an apparatus is positioned adjacent a site of the anatomical structure. The apparatus comprises an elongate flexible body including a proximal end, a distal end, and two hollow tubular members extending a length of the body and having two opposing distal cutting guide heads disposed at the distal end of the body and two proximal openings disposed at or near the proximal end of the body. The apparatus also comprises a flexible cutting member, where the distal end is adapted to receive an anatomical structure and a back and forth motion of the cutting member results in severing of the anatomical structure. Next, the cutting member is threaded into one tubular member through its proximal opening, through the tubular member, out its guide head, into the other tubular member through its guide head, through the other tubular member, and out it its proximal opening so that a portion of the cutting member is disposed on a top surface of the anatomical structure. Next, the apparatus is slid down the anatomical structure to a position at which the structure is to be cut. Next, the ends of the cutting member are pulled back and forth to cut into and through the anatomical structure at the position. Lastly, the apparatus and the anatomical structure are removed.

The present invention also relates to a method for harvesting a laterally extending anatomical structure of an animal including a human, the method comprising the step of making an incision in the animal or human at a convenient location to expose an anatomical structure to be harvested. After the incision is made, a distal end of an apparatus is positioned adjacent a site of the anatomical structure. The apparatus comprises an elongate flexible body including three tubular members extending a length of the body, each member having proximal openings. The body also includes the distal end comprising a suturing station. The suturing station comprises two opposing suturing heads, a suture guide channel extending from the suturing heads, and an arcuate suturing base between the suturing heads, where the base is adapted to receive an anatomical structure so that the suturing member loops around the structure, where the suturing member is designed to be threaded through the tubular aperture leading to the suturing station and fitted into the suture guide channel and across a top surface of the anatomical structure. The body also includes a cutting station comprising two opposing distal cutting guide heads. The distal end is adapted to receive an anatomical structure and a back and forth motion of the cutting member results in severing of the anatomical structure. The apparatus also includes a flexible cutting member and a flexible, bio-erodible or bio-degradable suturing member is threaded through the third tubular member forming a loop at the suturing station and tied off at one of the suturing heads with a slip knot. Next, the cutting member is threaded into one tubular member through its proximal opening, through the tubular member, out its guide head, into the other tubular member through its guide head, through the other tubular member, and out its proximal opening so that a portion of the cutting member is disposed on a top surface of the anatomical structure. Next, the apparatus is slid down the anatomical structure to a position at which the structure is to be cut. Next, the ends of the cutting member are pulled back and forth to cut into and through the anatomical structure at the position. Next, the suturing member is pulled at its proximal end extending out of the proximal opening of the third tubular member so that the loop tightens on the anatomical structure suturing the structure at the suturing station. Lastly, the apparatus and the anatomical structure are removed.

Suitable material out of which the apparatus of this invention can be made includes, without limitation, any flexible material that is approved for use in an animal or human body. Moreover, the handle part of the apparatus can be inflexible or less flexible than the tubular members. Exemplary materials include plastics, rubbers, metals or combinations of these materials provided that the material is approved for use in animals or humans.

Suitable material out of which the cutting member of this invention can be made includes, without limitation, any high tensile strength material that can be made into a wire or continuous filament. Exemplary materials include metallic wires, synthetic or natural fibrous materials commonly used in medicine. The wires or filaments can be smooth or rough or textured to improve cutting efficiency. The wires or filaments can be differentially textured so that a portion of the wire or filament will cut the anatomical structure (e.g., tendon, muscle, nerve, vessel, etc.).

Suitable material out of which the suturing member of this invention can be made includes, without limitation, any suturing material now known or will be invented in the future. Exemplary materials include natural sutures made of collagen from intestines of mammals or from synthetic collagen (polymers) or other synthetic polymers that have been approved by the FDA for use in animals including humans.

Figures 2A, 2B, 2C:
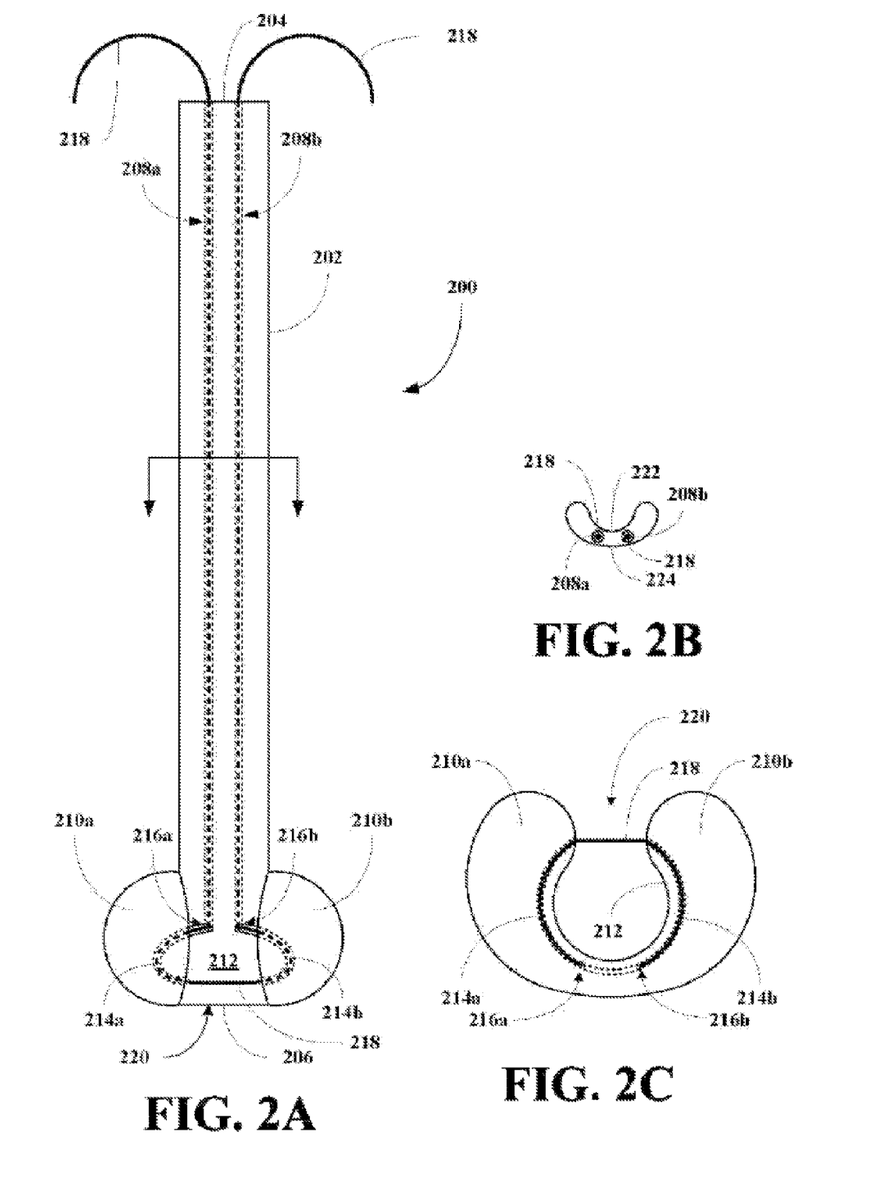
FIGS. 2A-C depict different views of an embodiment of a harvesting apparatus of this invention including a cutting distal end.
Figure 3A:
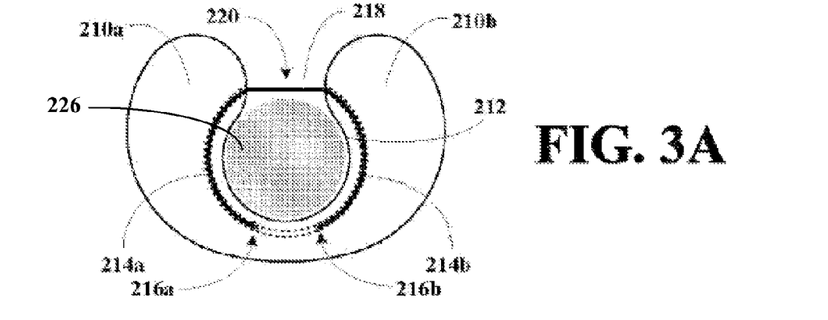
FIGS. 3A-D depict a cutting process of an anatomical structure positioned in a distal end of an apparatus of this invention.
Figure 3B:
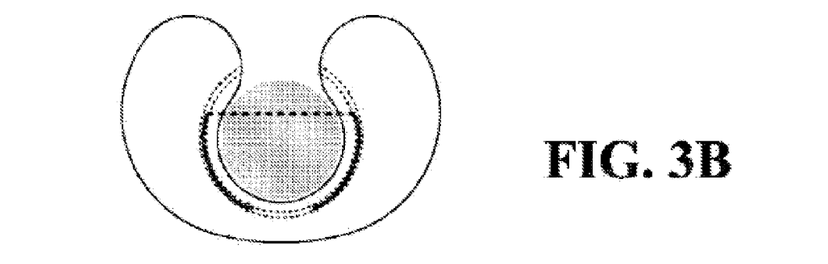
Figure 3C:
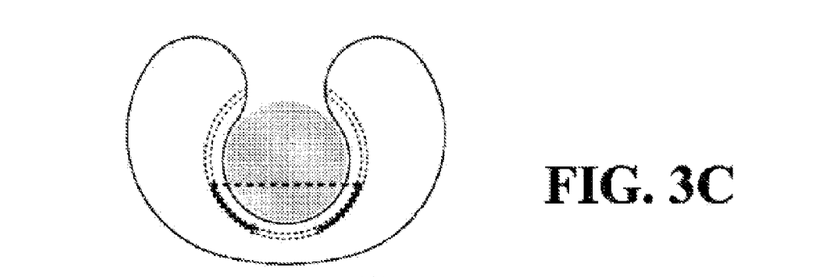
Figure 3D:
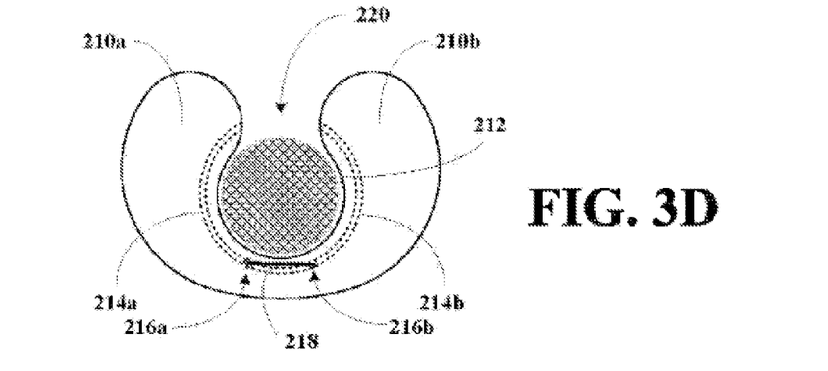

Referring now to FIGS. 2A-C, an embodiment of an apparatus of this invention, generally 200 is shown to include an elongate member 202 having a proximal end 204 and a distal end 206. The elongate member 202 includes two tubular apertures 208*a*& *b* extending from the proximal end 204 to the distal end 206. The proximal end 204 can also include two leg sections (shown in the attachment) having feet, where the two tubular apertures terminate. The distal end 206 includes two opposing heads 210*a*& *b* and an arcuate base 212 interposed therebetween. The heads 210*a*& *b* include cutting guide channels 214*a*& *b* having bases 216*a*& *b* coincident with the distal ends of the tubular apertures 208*a*& *b*. The apparatus 200 also includes a flexible cutting member 218, which passes through the tubular apertures 208*a* from the proximal end 204 of the apparatus 100 to the base 216*a*. The member 218 then follows the guide channel 214*a*, then across a gap 220 between the heads 210*a* and 210*b*. The member 218 then follows the channel 214*b* into the base 216*b*, through the aperture 208*b* and out the proximal end 204 of the apparatus.

Looking at FIG. 2B, the member 202 can have a concave top surface 222 and a convey bottom surface 224 adapted to engage an anatomical structure.

Referring now to FIGS. 3A-D, the apparatus 200 of FIGS. 2A-C is shown in a series of views of the apparatus 200 cutting through an anatomical structure 226.

Figure 4:
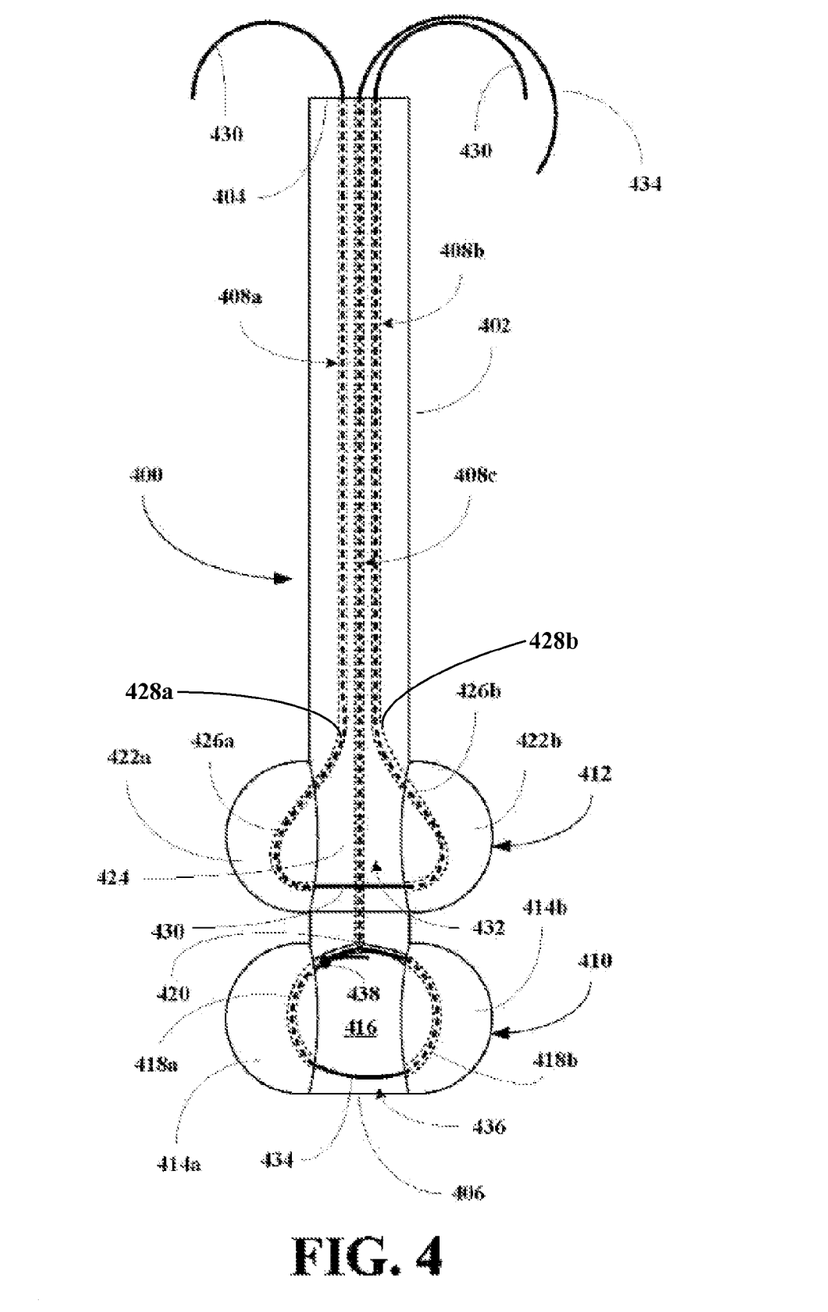
FIG. 4 depicts another embodiment of a harvesting apparatus of this invention including a suturing station and cutting station at the distal end of the apparatus.

Referring now to FIG. 4, another embodiment of an apparatus of this invention, generally 400 is shown to include an elongate member 402 having a proximal end 404 and a distal end 406. The elongate member 402 includes three tubular apertures 408a-c extending from the proximal end 404 to the distal end 406. The proximal end 404 can also include two leg sections (shown in the attachment) having feet, where the two tubular aperture terminate. The distal end 406 includes a suturing station 410 and a cutting station 412. The suturing station 410 includes two opposing suturing station heads 414a& b and an arcuate base 416 interposed therebetween. The suturing station heads 414a& b include suturing guide channels 418a& b having a base 420 coincident with the distal end of the tubular aperture 408c. The cutting station 412 includes two opposing cutting station heads 422a& b and an arcuate base 424 interposed therebetween. The cutting station heads 422a& b include cutting guide channels 426a& b having bases 428a& b coincident with the distal ends of the tubular apertures 408a& b. The apparatus 400 also includes a flexible cutting member 430, which passes through the tubular aperture 408a from the proximal end 404 of the apparatus 400 to the base 428a. The cutting member 430 then follows the guide channel 426a, then across a gap 432 between the heads 422a and 422b. The cutting member 430 then follows the channel 426b into the base 428b, through the aperture 408b and out the proximal end 404 of the apparatus. The apparatus 400 also includes a flexible suturing member 434, which passes through the tubular aperture 408c from the proximal end 404 of the apparatus 400 to the base 420. The suturing member 434 then follows the guide channel 418a, then across a gap 436 between the heads 414a and 414b. The suturing member 434 then follows the channel 418b past the base 420 and a slip knot 438 is formed and pushed into the channel 418a. The suturing member 434 is designed to be pulled so that the loop formed by the slip knot 438 tightens about an anatomical structure to suture the structure above the position where it will be cut.

Referring now to FIGS. 5A-E, another embodiment of an apparatus of this invention, generally 500, is shown to include an elongate member 502 having a distal end 504 and a proximal end 506 comprising a handle 508. The elongate member 502 also includes two hollow tubular members 510a& b. The tubular members 510a& b include proximal end portions 512a& b and distal end portions 514a& b. The proximal end portions 512a& b include flared openings 516a& b, and similarly, the distal ends 514a& b include flared openings 518a& b. The two flared openings 518a& b face each other, while the two flared openings 516a& b point away from each other.

Figure 5A:
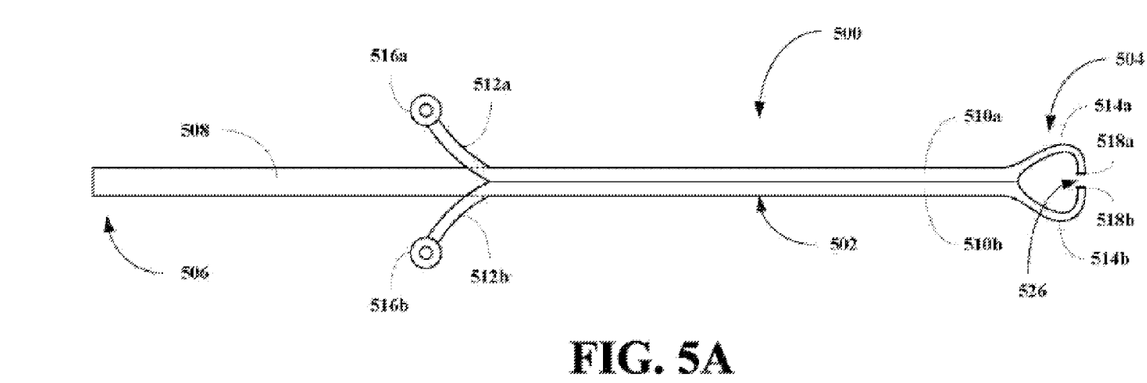
FIGS. 5A-E depict another embodiment of harvesting apparatus of this invention and a cutting process of an anatomical structure positioned in a distal end of the apparatus.
Figure 5B:
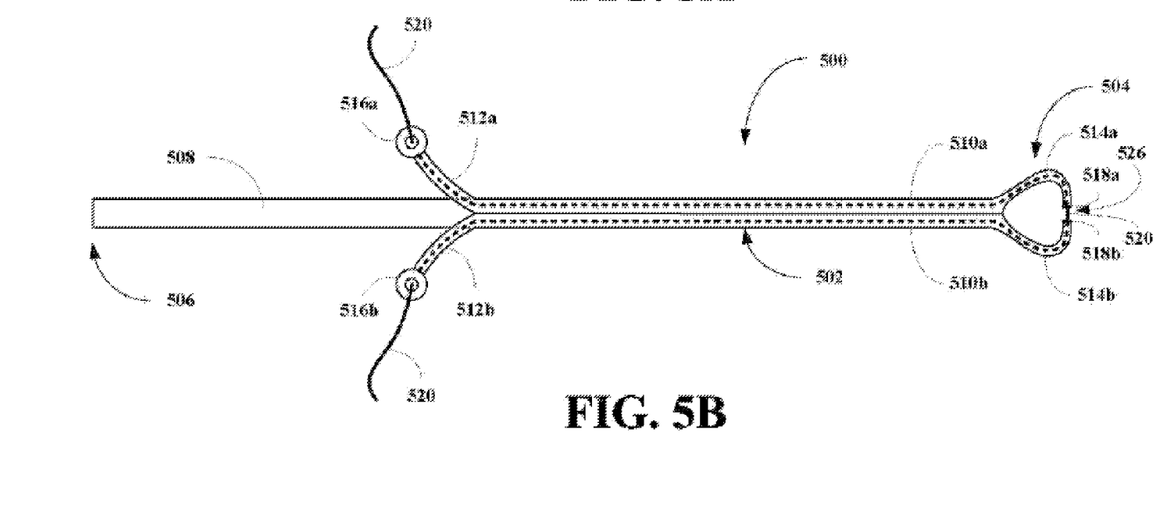

Looking at FIG. 5B, a cutting member 520 is designed to be threaded into the opening 516a or 516b, through the tubular member 510a or 510b, out of the distal end opening 518a or 518b, into the distal end opening 518b or 518a, through the tubular members 510b or 510a and out the proximal end opening 516b or 516a, respectively. In this way, the cutting member 520 is disposed across the distal ends 514a& b of the tubular member 510a& b.

Figure 5C:
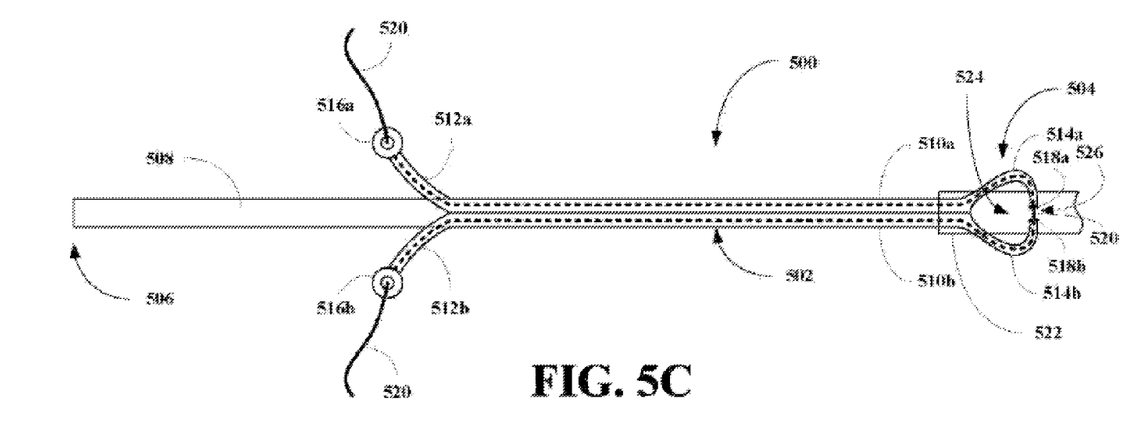

Looking at FIG. 5C, the distal end 504, with the cutting member 520, is slid onto a tendon 522 so that the tendon 522 is inside a cutting zone 524 of the apparatus 500 defined by the curved distal ends 514a& b of the tubular members 508a& b.

Figure 5D:
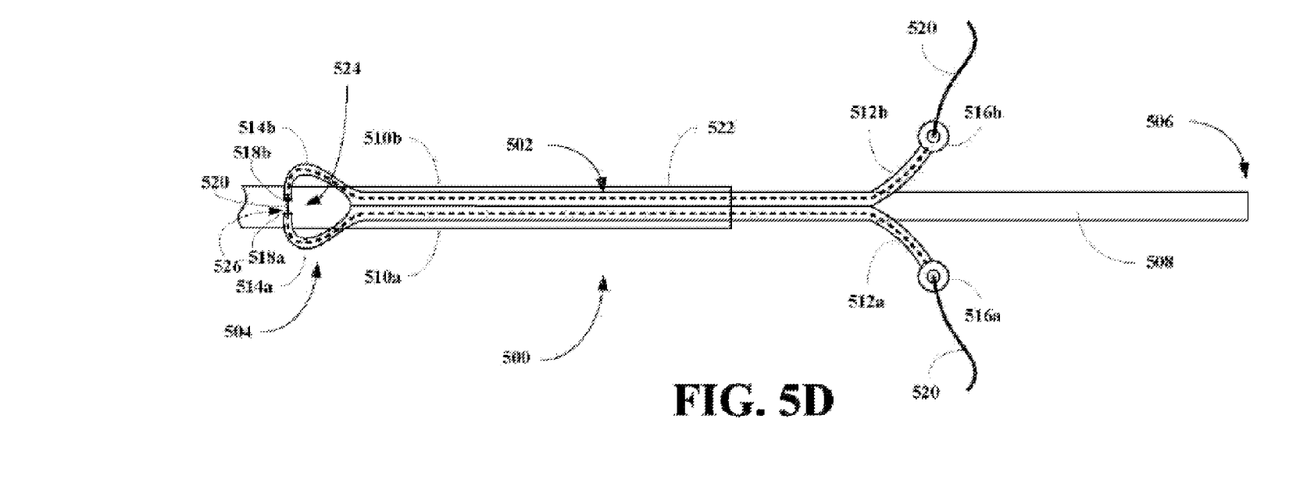

Looking at FIG. 5D, the apparatus 500, with the assistance of the handle 506, is slid down the tendon 520 to a desired location.

Figure 5E:
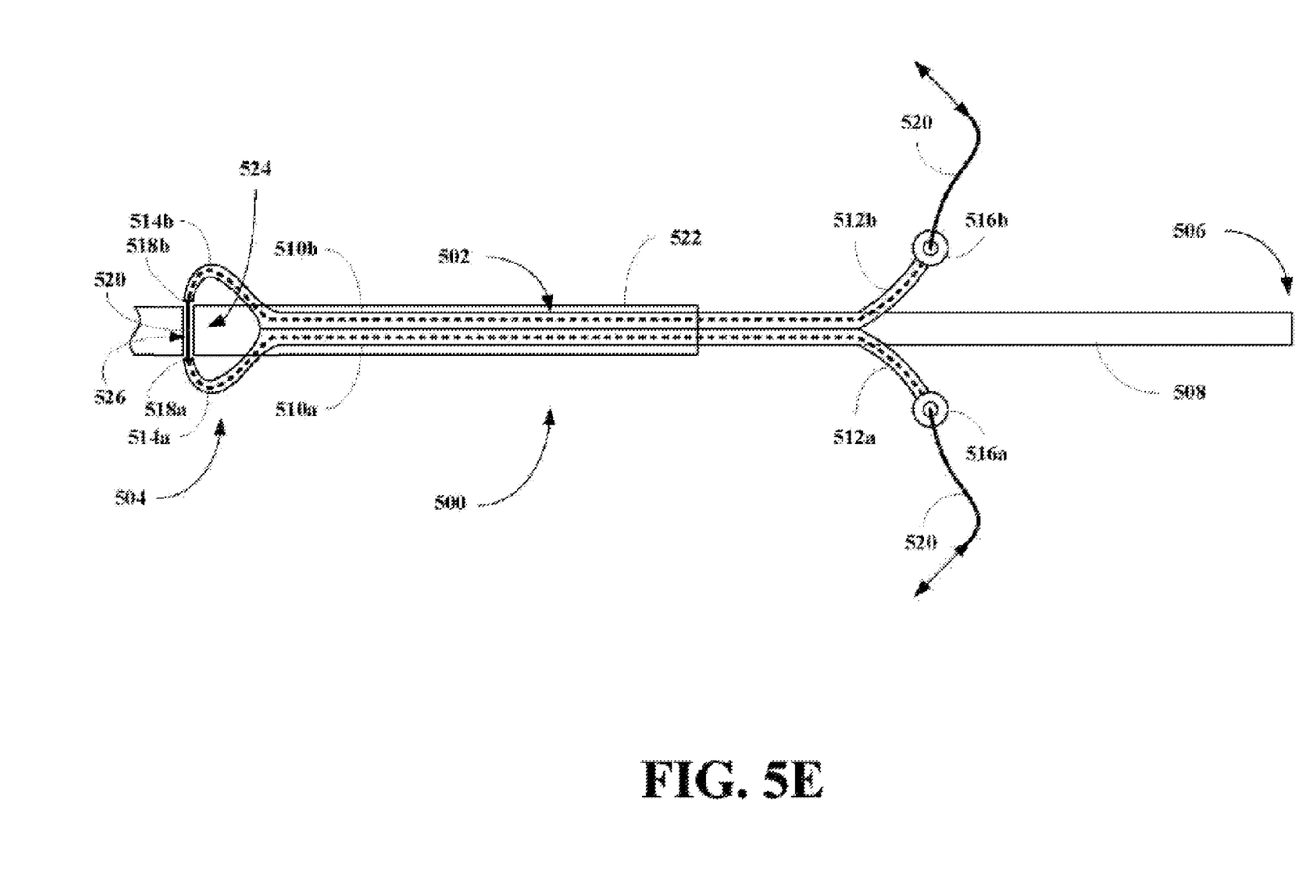

Looking at FIG. 5E, the cutting member 520 is then pulled back and forth to cut the tendon 522 at the location within the cutting zone 524. The distal end portions 514a& b of the tubular members 510a& b are flexible so that the end portions 514a& b can separate further during the tendon cutting process. Cutting is achieved because the cutting zone 524 is designed to be flat.

Alternatively, the apparatus 500 can be slid down a tendon and once the cutting location along the tendon is located, the cutting member 520 can be threaded through the tubular members 510a& b. With the cutting member 520 in place, the tendon can then be cut as shown in FIG. 5E. Although a gap 526 is shown between the flared distal openings 518a& b, the gap can be really small so that the cutting member 520 can be threaded through the tubular members 510a& b without an opportunity for the cutting member 520 to miss the facing opening.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. An apparatus for severing an anatomical structure, comprising:
    a single elongate body having a longitudinal axis, including:
        a proximal end,
        a distal end,
        two parallel tubular members, each tubular member extending a length of the body parallel to the longitudinal axis and each having a distal opening disposed at the distal end of the body and a proximal opening disposed at or near the proximal end of the body, wherein the distal openings are opposed perpendicularly to the longitudinal axis, and
    a flexible cutting member adapted to be threaded into one tubular member through its proximal opening, out its distal opening, into the other tubular member through its distal opening, and out its proximal opening, such that the flexible cutting member is parallel to the longitudinal axis in the tubular members and is perpendicular to the longitudinal axis between the distal openings,
    wherein the distal end is adapted to receive an anatomical structure, and wherein the distal end is adapted sever the anatomical structure using the cutting member.

2. The apparatus of claim 1, further comprising an arcuate base adapted to receive the anatomical structure.

3. The apparatus of claim 1, wherein the distal openings are angled so that a top of the distal openings is more distal than a bottom of the distal openings to increase cutting efficiency.

4. The apparatus of claim 1, wherein a surface of the body is curved to aid the body in following the anatomical structure to the point where the structure is to be cut.

5. The apparatus of claim 1, wherein the proximal end of the body comprises a handle.

6. The apparatus of claim 1, wherein the anatomical structure is a tendon, a slender muscle, a long nerve filament or bundle, a vessel, or a laterally extended anatomical structure.

7. The apparatus of claim 1, further comprising:
    a fiber optic system for viewing the positioning of the distal end of the apparatus, an X-ray opaque element for X-ray monitoring of distal end positioning,
an ultrasound reflective element for ultrasound monitoring of distal end position, or
a monitor for monitoring an environment in the distal end.

8. A harvesting apparatus comprising:
an elongate flexible body including:
   first, second, and third tubular members extending a length of the body, each member having a proximal opening,
   a distal end comprising:
      a suturing station comprising:
         two opposing suturing heads,
         a suture guide channel extending from the suturing heads, and
      a cutting station comprising two opposing distal cutting guide heads,
a flexible cutting member adapted to be threaded into the second tubular member through its proximal opening, out its guide head, into the third tubular member through its guide head, and out its proximal opening, wherein the distal end is adapted to receive an anatomical structure and a back and forth motion of the cutting member results in severing of the anatomical structure, and
a flexible, bio-erodible or bio-degradable suturing member adapted to be threaded into the first tubular member leading to the suturing station and fitted into the suture guide channel and forming a loop at the suturing station and tied off at one of the suturing heads with a slip knot so that when the suturing member is pulled at its proximal end extending out of its proximal opening, the loop will tighten on the anatomical structure suturing the structure at the suturing station.

9. The apparatus of claim 8, wherein the cutting station further comprises opposing cutting channels.

10. The apparatus of claim 8, wherein the cutting station further comprises an arcuate base between the two guide heads adapted to receive the anatomical structure.

11. The apparatus of claim 9, wherein the cutting channels are angled so that a top of the cutting channel is more distal than a bottom of the cutting channel to increase cutting efficiency.

12. The apparatus of claim 8, wherein a top surface of the body is curved to aid the body in following the anatomical structure to the point where the structure is to be cut.

13. The apparatus of claim 8, wherein the proximal end of the body comprises a handle.

14. The apparatus of claim 8, wherein the anatomical structure is a tendon, a slender muscle, a long nerve filament or bundle, a vessel, or a laterally extended anatomical structure.

15. The apparatus of claim 8, further comprising:
A fiber optic system for viewing the positioning of the distal end of the apparatus,
an X-ray opaque element for X-ray monitoring of distal end positioning,
an ultrasound reflective element for ultrasound monitoring of distal end position, or
a monitor for monitoring an environment in the distal end.

16. The apparatus of claim 1, wherein the two tubular members are adjacent in the body.

17. The apparatus of claim 8, wherein the first, second, and third tubular members are adjacent in the body.

18. The apparatus of claim 8, wherein the first, second, and third tubular members are parallel.

* * * * *